United States Patent
Robinson, Jr.

(10) Patent No.: US 6,426,212 B1
(45) Date of Patent: Jul. 30, 2002

(54) BIOLOGICAL CONDUCTIVITY TESTING CELL

(76) Inventor: William L. Robinson, Jr., 2517 Quantico Ave., Baltimore, MD (US) 21215

(*) Notice: Subject to any disclaimer, the term of this patent is extended or adjusted under 35 U.S.C. 154(b) by 0 days.

(21) Appl. No.: 09/934,564

(22) Filed: Aug. 23, 2001

(51) Int. Cl.[7] .............................................. C12M 1/35
(52) U.S. Cl. ............................... 435/288.1; 435/287.1; 156/153
(58) Field of Search ........................... 435/287.1, 288.1, 435/289.1; 204/400, 403; 156/150, 153

(56) References Cited

U.S. PATENT DOCUMENTS 6,001,617 A * 12/1999 Raptis ...................... 435/173.1

* cited by examiner

Primary Examiner—David A. Redding
(74) Attorney, Agent, or Firm—Peter Gibson

(57) ABSTRACT

Improved adhesion of platinum (Pt) alloy electrode deposition upon end surfaces of a cylindrical glass biological conductivity testing cell with mechanical resistance and chemical purity is obtained with removal of glass surface material in areas of Pt alloy deposition. Removal of surface material from the entire area of Pt alloy deposition by abrasion to a depth equivalent to the thickness of the deposition immediately prior to Pt alloy deposition obtains:

(a) a chemically virgin surface without contaminants;
(b) a uniform surface variation resisting shear displacement of the electrode;
(c) disposition of the resulting electrode wholly within the overall cylindrical cell dimensions;
(d) elimination of exposed edges of the electrode.

Grooves effected with rotary abrasion upon interior and exterior end surfaces which are evenly spaced radially and axially with respect to the cylindrical structure provide resistance to displacement of the Pt alloy film. Even removal of glass surface material radially and axially with respect to the cylindrical structure preserves the electrical characteristics of the electrodes and the testing cell overall. An annular groove located at the electrode edges obviates shear forces upon this most critical area.

30 Claims, 5 Drawing Sheets

BIOLOGICAL CONDUCTIVITY TESTING CELL

BACKGROUND OF THE INVENTION

1. Field of the Invention

The present invention relates: generally to biological conductivity testing cells possessing a substantially cylindrical structure; more particularly to biological conductivity testing cells possessing a substantially cylindrical structure with two opposed Pt alloy electrodes disposed upon either end; and most specifically to biological conductivity testing cells possessing a substantially cylindrical structure with two opposed Pt alloy electrodes disposed upon either end intended for passage of a weak alternating current therethrough for the obtainment of impedance measurements.

2. Prior Art

Biological conductivity testing cells possessing a substantially cylindrical structure with two opposed Pt alloy electrodes disposed upon either end intended for passage of a weak alternating current therethrough are considered to be well known. With regard to the present innovation the prior art is considered to be restricted to simple deposition of Pt alloy upon equivalent areas with regard to either end including interior, exterior, and end surfaces.

Figure 1:
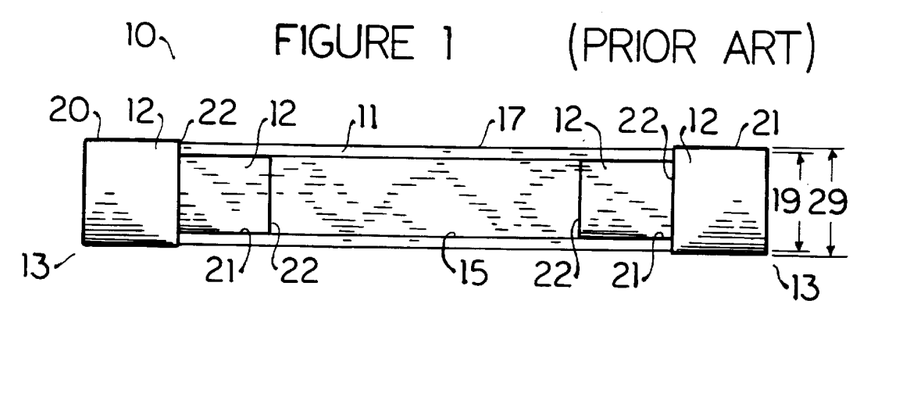
FIG. 1 is a plain elevational view taken from a side of a conventional, prior art, biological conductivity testing cell comprised of a glass cylinder with two opposed electrodes at either end.
Figure 2:
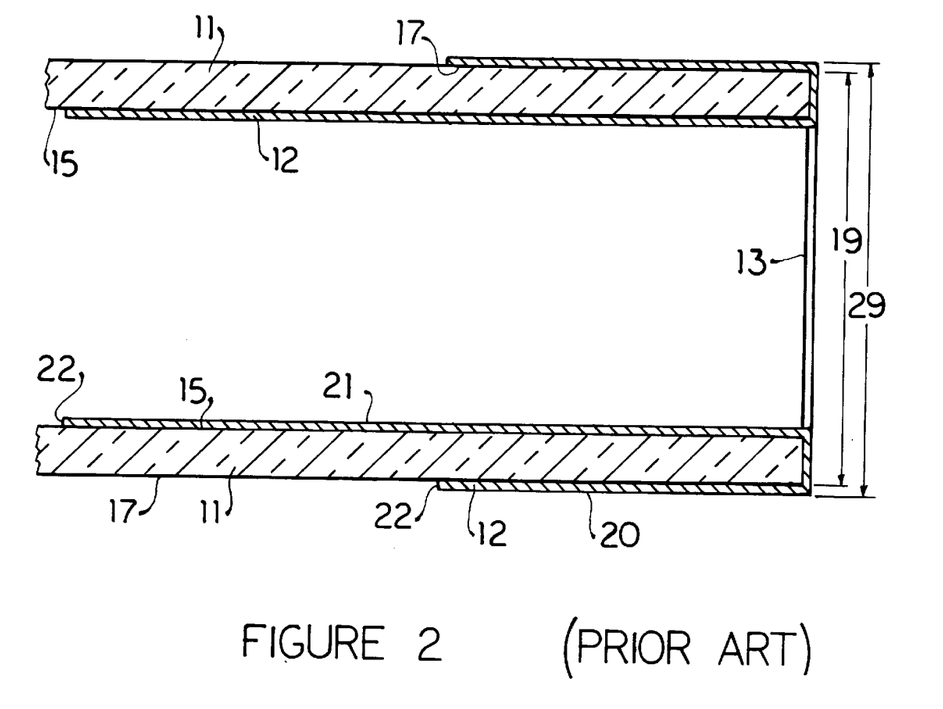
FIG. 2 is a cross sectional detail view of an end of one of the electrodes upon the glass cylinder of the conventional, prior art, biological conductivity testing cell depicted in FIG. 1.

FIG. 1 depicts a conventional conductivity testing cell 10 made of a glass cylinder 11 and two opposed electrodes 12 between which a weak alternating current in passed through a biological sample held therein for measuring changes in impedance associated with metabolic activity inclusive of cell division and genetic replication. FIG. 2 depicts in detail an end of the conventional conductivity testing cell 10 depicted in FIG. 1 inclusive of a portion of the glass cylinder 11 and an electrode 12 with exposed interior and exterior surfaces 21, 20 resulting from the simple deposition of the Pt alloy which are both offset with respect to the adjacent exposed glass interior and exterior surfaces 15, 17, and necessarily present an exposed edge 22 of the electrode 12 which is subject to shear. It is further seen that the covered glass interior and exterior surfaces 15, 17 under the electrode 12 are the same as the adjacent exposed glass surfaces 15, 17.

Conventional conductivity testing cells 10 made of a glass cylinder 11 possessing two opposed electrodes 12 between which a weak alternating current is passed through a biological sample held therein must be autoclaved between tests in order to assure sterility prior to introduction of a new biological sample. Repeated autoclaving results in separation of the Pt alloy deposition comprising the electrodes 12 from the underlying glass interior and exterior surfaces 15, 17. Serious deterioration of the electrode 12 resulting from shear during autoclaving is typically experienced after only three cycles of using the testing cell 10.

The electrodes 12 must be Pt alloy because platinum possesses unique characteristics with regard to electro-chemical activity: platinum, alone among all the elements, acts as a pure catalyst for electro-chemical activity without loss of material and without other undesired activity. It is noted that the portions of the electrodes 12 disposed interiorly in conventional conductivity testing cells 10 comprised of a glass cylinder 11 as depicted in FIG. 1 extend inwardly much further than the portions of the electrodes 12 disposed exteriorly. This is because the exterior portion makes electrical contact with a metal conductor while the interior portion facilitates the conductance of electrical current through a water based biological sample and a greater surface area is required to support the conductance of the electrical current across the interface with this inherently less conductive medium.

Statement of Need

With a current cost of approximately twice that of gold platinum is considered relatively expensive. Platinum has many industrial uses including laboratory glassware and catalytic converters necessary to $NO_x$ reduction from internal combustion engine exhaust. It is not anticipated that the cost of platinum will be greatly reduced in near future owing to anticipated demand. While the amount of platinum in the Pt alloy deposition upon a conventional biological conductivity testing cell is measured in grams a degraded electrode 12 cannot be repaired without return of the testing cell for complete removal and redeposition of the Pt alloy and conductivity test cells 10 are hence routinely discarded after deterioration of one of the electrodes 12.

Therefore, the entire cost of the conductivity test cell 10 must be amortized over an average of approximately three tests, including the cost of manufacturing the glass cylinder 11, the platinum in the Pt alloy deposition, the process of deposition, transportation, and all other expenses associated with getting a product to market. While the cost of replacing a conductivity test cell 10 after an average of three tests may be acceptable in research it is recognized that this cost is inhibitive of clinical usage wherein millions of tests annually are anticipated. A need is hence discerned for a means of increasing the number of tests a biological conductivity test cell 10 can be utilized prior to deterioration of the electrodes 12.

SUMMARY OF THE INVENTION

Objects of the Invention

The encompassing object of the principles relating to the present invention is a biological conductivity testing cell with a platinum alloy electrode upon each of two opposed ends of a glass cylinder which is relatively unaffected by autoclaving.

A first auxiliary object of the principles relating to the present invention is the provision of a chemically pure surface upon end surfaces of a glass cylinder intended for deposition of platinum alloy thereby eliminating contamination.

A second auxiliary object of the principles relating to the present invention is the provision of a uniform surface roughness upon end surfaces of a glass cylinder intended for deposition of platinum alloy for resisting shear.

A third auxiliary object of the principles relating to the present invention is the provision of platinum alloy upon the two opposed ends of a glass cylinder wholly within the overall cylindrical cell dimensions thereby eliminating all exposed edges of the deposition.

A fourth auxiliary object of the principles relating to the present invention is the provision of radially and axially uniform etching upon end surfaces of a glass cylinder intended for deposition of platinum alloy for resisting shear.

A fifth auxiliary object of the principles relating to the present invention is the provision of evenly spaced grooves annular upon end surfaces of a glass cylinder intended for deposition of platinum alloy for resisting shear.

Ancillary objects of the principles relating to the present invention include the preservation of desired electrical characteristics of the electrodes comprised of the deposition of platinum alloy upon the end surfaces of a glass cylinder in use as a biological conductivity testing cell for the measurement of impedance of a weak alternating current passed through a biological sample contained therein and the utilization of a greater interior surface area relative the exterior surface area of each end of the glass cylinder for deposition of platinum alloy thereupon.

Principles Relating to the Present Invention

In achievement of the above stated objectives it is suggested that removal of glass surface material by abrasion from the end surface areas of a glass cylinder intended for deposition of platinum alloy prior to deposition be effected. If the entire surface area intended for deposition thereupon is abraded with a chemically inert abrading material immediately prior to deposition of the platinum alloy a chemically pure, virgin, surface is obtained and all potential contaminates which could later cause separation eliminated.

Utilization of an appropriate abrasion also achieves a uniform surface roughness also provides resistance to shear. With a uniform removal of glass surface material from the entire area intended for platinum deposition to a depth equivalent to the thickness of the coating deposited thereafter a substantially continuous exterior surface of electrode and exposed glass surface is obtained and exposed edges of electrode are avoided and separation from shear acting upon exposed edges eliminated.

Selective removal of glass surface material in an annulus located at the edge of the intended platinum deposition will also, regardless of other removal of glass material from the other areas of the deposition surface, ensure elimination of exposed electrode edges and separation from shear acting upon the same. Annular grooves located at consistent axial intervals with regard to both ends of the glass cylinder in the deposition area will provide physical resistance to axial shear displacement of the platinum deposition without adversely affecting the electrical characteristics of the biological conductivity testing cell.

Similarly, axial grooves located at consistent radial intervals with regard to the glass cylinder in the deposition area will provide physical resistance to radial shear displacement of the platinum deposition without adversely affecting the electrical characteristics of the biological conductivity testing cell. And a helical diamond pattern of grooves located at consistent intervals in the deposition area will provide physical resistance to both axial and radial shear forces without adversely affecting the electrical characteristics of the biological conductivity testing cell. These grooves can be in addition to a uniform removal of glass surface material.

It is recommended in all cases that removal of glass surface material from the two end areas of the glass cylinder intended for deposition of platinum alloy be effected with appropriate abrasion using an inert abrading material. The grain size is determinative of the resulting roughness of the surface abraded. Regardless of the specific type of glass utilized, and borosilicate glasses are considered satisfactory, silicon carbide grinding wheels are suggested for abrading any grooves.

A small diameter silicon carbide cylinder is suggested for effecting a uniform removal of glass surface material from the concave interior cylindrical surfaces and a large diameter silicon carbide wheel is suggested for the convex exterior surfaces. The axes of the glass and silicon carbide cylinders are in both cases parallel. Abrasive cloth is also suggested for the convex exterior surfaces and the end surfaces, which are flat, are preferably abraded with an opposed flat surface which could be moving, as presented by a belt, or stationary, with linear or rotary displacement of the glass cylinder in compression against the flat abrading surface.

Use of conventional vapor deposition techniques and conventional platinum alloys including iridium, osmium, rhodium, rhenium, and ruthenium are recommended although it is noted that the last two, at 5.5% and 4% the conductivity of copper, which compare with 16% for pure platinum, are low compared with the other alloys. A platinum iridium alloy of between 5 to 30 percent iridium is preferred for superior conductivity.

Other aspects regarding preferred manners of making and using an embodiment in accordance with the principles relating to the present invention may be appreciated in a reading of the detailed description further below, particularly if made with reference to the drawings attached hereto, and described briefly directly below.

| Nomenclature | | | |
|---|---|---|---|
| 10 | testing cell | 11 | glass cylinder |
| 12 | electrode | 13 | glass end surface |
| 15 | glass interior surface | 17 | glass exterior surface |
| 19 | glass cylinder diameter | 20 | electrode exterior surface |
| 21 | electrode interior surface | 22 | electrode edge |
| 23 | prepared end surface | 25 | prepared interior surface |
| 27 | prepared exterior surface | 29 | diamter of electrode |
| 30 | helical etching | 31 | axial etching |
| 32 | radial etching | 33 | annular groove |
| 35 | valley | 37 | peak |
| 39 | surface removal depth | 40 | deposition thickness |

DETAILED DESCRIPTION OF A PREFERRED EMBODIMENT

Figure 3:
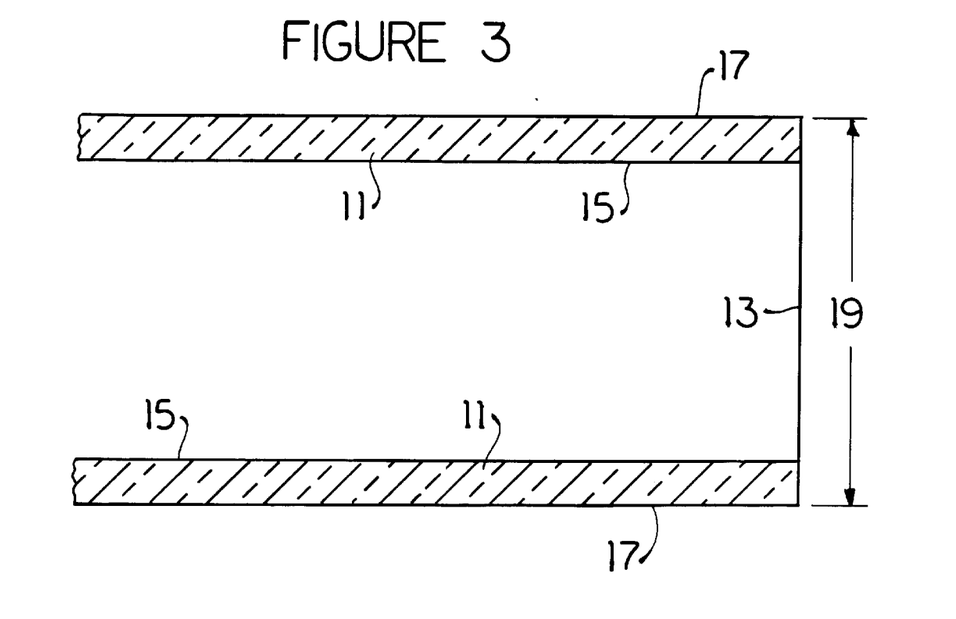
FIG. 3 is a cross sectional detail view taken from an end of a glass cylinder prior to surface preparation in accordance with the principles relating to the present invention.

FIGS. 1 & 2 have been referenced above in discussion of the prior art wherein a biological conductivity testing cell 10 comprised of a glass cylinder 11 and two opposed electrodes 12 each comprised of a platinum alloy coating deposited upon one glass end surface 13, and adjacent areas of the glass interior surfaces 15 and glass exterior surfaces 17. It is recognized that the glass cylinder diameter 19 is exceeded by the electrode diameter 29 and that the electrode edges 22 are consequently exposed and subject to shear. FIG. 3 depicts an end of a glass cylinder 11 alone which is substantially similar to the glass cylinder 11 depicted in FIG. 1 prior to surface preparation prior to platinum alloy deposition in accordance with the principles relating to the present invention. It is noted that the glass exterior surface 17 is uniform as is the glass interior surface 15.

Figure 4:
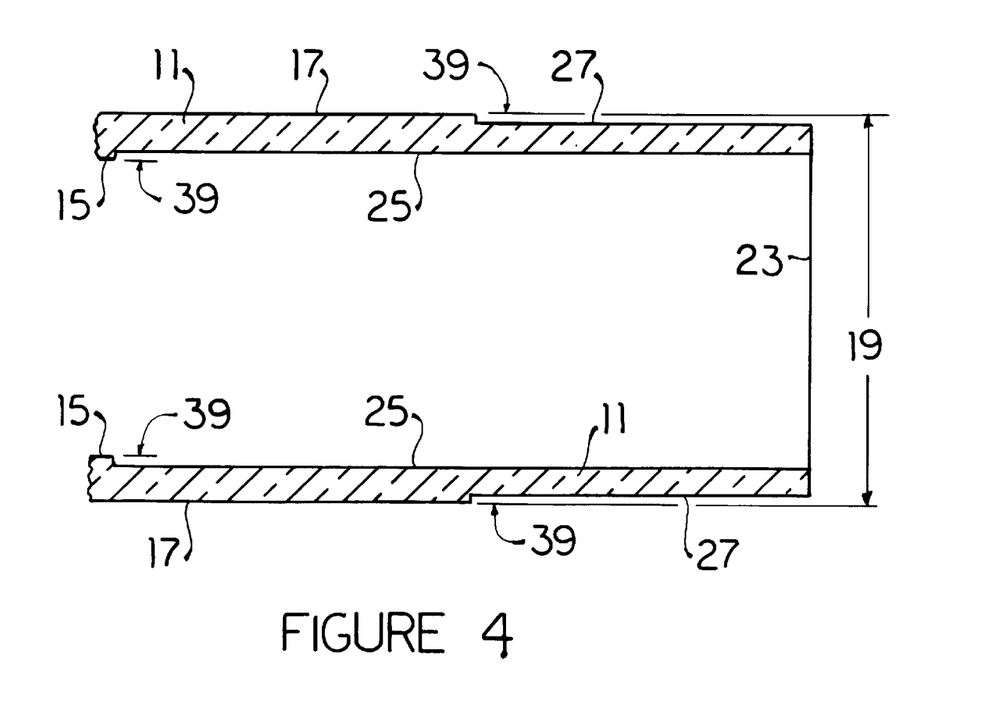
FIG. 4 is a cross sectional detail view taken from an end of a glass cylinder prepared in accordance with the principles relating to the present invention prior to platinum alloy deposition.

FIG. 4 depicts in detail the end of the glass cylinder 11 depicted in FIG. 3 having a prepared end surface 23, prepared interior surface 25, and a prepared exterior surface 27 wherein it is seen that these prepared surfaces 23, 25, 27 have had glass surface material removed resulting in an offset from the original glass cylinder end, interior, and exterior surfaces 13, 15, 17. It is preferred that the glass surface material be removed by abrasion as discussed above in summary of the invention wherein it was recommended that a silicon carbide cylinder be utilized to abrade the glass interior surfaces 15, a silicon carbide wheel or abrasive cloth be utilized for the glass exterior surfaces 17, and a flat abrasive surface either moving or stationary be utilized for abrasion of the glass end surface 13. It is also emphasized that this abrasion in preparation of these surfaces 13, 15, 17 be done immediately prior to vapor deposition of platinum alloy in creation of the electrodes 12 in order to minimize the likelihood of contamination.

Figure 5:
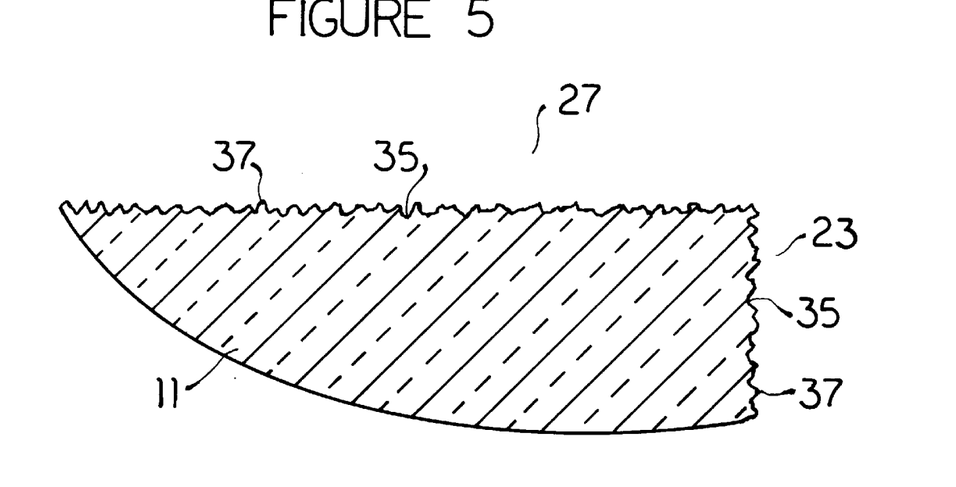
FIG. 5 is a magnified cross sectional detail view of taken from an end corner of a glass cylinder prepared in accordance with the principles relating to the present invention prior to platinum alloy deposition depicting the uniformly rough and virgin deposition surface resulting from removal of glass surface material.

FIG. 5 depicts a magnified detail view of the top corner of the glass cylinder 11 with a prepared exterior surface 27 in which the uniform roughness effected by appropriate abrasion in accordance with the principles relating to the present invention is clearly seen. The magnitude of the peaks 37 and valleys 35 seen to have been effected in this prepared exterior surface 27 is commensurate with the size of the grain utilized in abrasion. It is intended that the magnitude of these peaks 37 and valleys 35 be less than, but not more than an order of magnitude less than, the deposition thickness 40 of the platinum alloy coating thereupon comprising an electrode 12 in order to ensure full encasement by the electrode 12 and substantial resistance to shear in displacement of the same from the underlying glass cylinder 11.

It is also noted with respect to the preparation of the glass end, interior, and exterior surfaces 13, 15, 17 depicted in FIGS. 3–5 by abrasion that the glass surface material removed is of substantially uniform depth and is wholly contiguous. It is preferred that every surface upon which platinum alloy is to be deposited first be freshly abraded to expose uncontaminated virgin glass in order to avoid separation of the electrode 12 from the glass cylinder 11 owing to contamination in addition to providing physical resistance against shear with a rough underlying surface.

Figure 6:
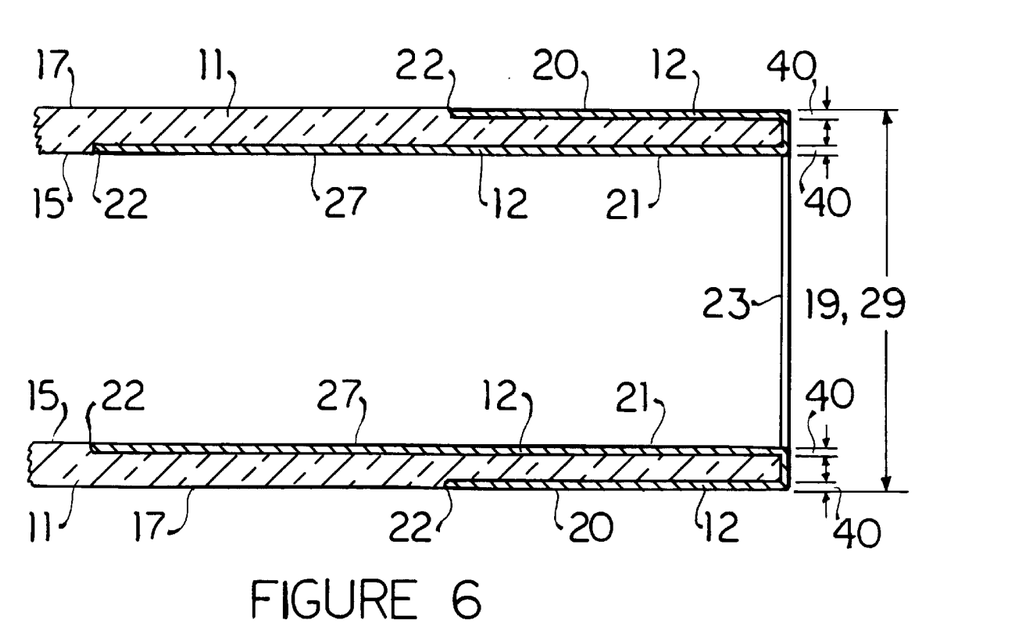
FIG. 6 is a cross sectional detail view taken from an end of biological conductivity testing cell in accordance with the principles relating to the present invention having platinum alloy deposited upon prepared exterior, end, and interior surfaces.

It is preferred that the glass surface material be removed, as depicted in FIG. 4, to a substantially uniform surface removal depth 39 approximately equal to the thickness of the platinum alloy deposition comprising the electrode 12 so that, as seen in FIG. 6, the electrode exterior and interior surfaces 20, 21 are substantially flush with the adjacent, unprepared, glass exterior and interior surfaces 17, 15. It is also preferred that all of the prepared interior and exterior surfaces 25, 27 be utilized as a deposition surface for a platinum alloy coating comprising the electrode 12 so that the electrode edges 22 are hidden as seen in FIG. 6 and are not subject to shear.

It is noted that if the deposition thickness 40 of the platinum alloy comprising the electrode 12 is exceeded by the surface removal depth 39 the electrode edge 22 is effectively shielded from shear and that a substantially flush relation between the electrode interior or exterior surface 21, 20 and the adjacent, unprepared, glass interior or exterior surface 15, 17 is actually the limit of the preferred case wherein the deposition thickness 40 of the platinum alloy comprising the electrode 12 is exceeded by the surface removal depth 39 and the resulting electrode interior or exterior surface 21, 20 does not extend beyond, inwardly or outwardly respectively to, the adjacent unprepared glass interior or exterior surface 15, 17.

Figure 7:
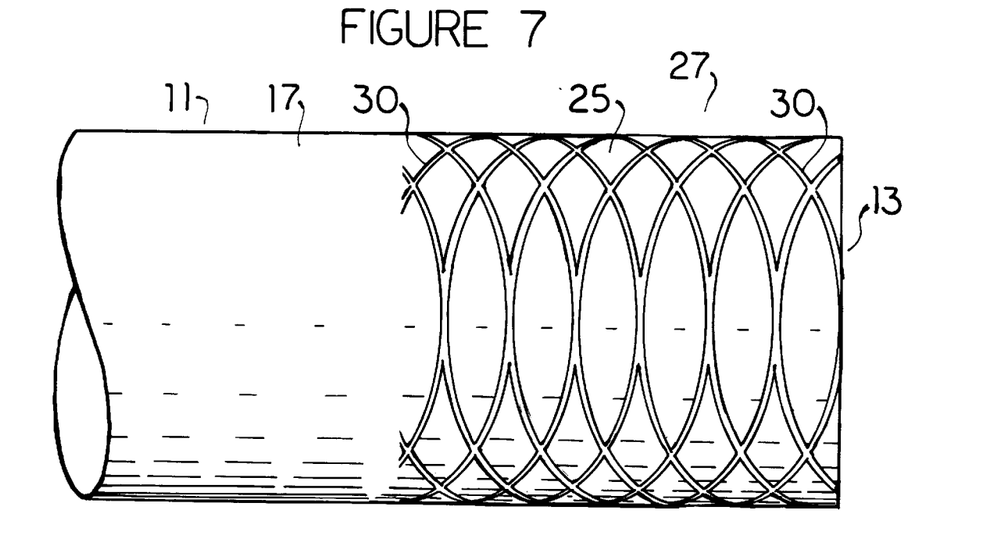
FIG. 7 is a plain elevational view taken of an end of a glass cylinder with the exterior surface prepared in accordance with the principles relating to the present invention with a diamond pattern of grooves.
Figure 8:
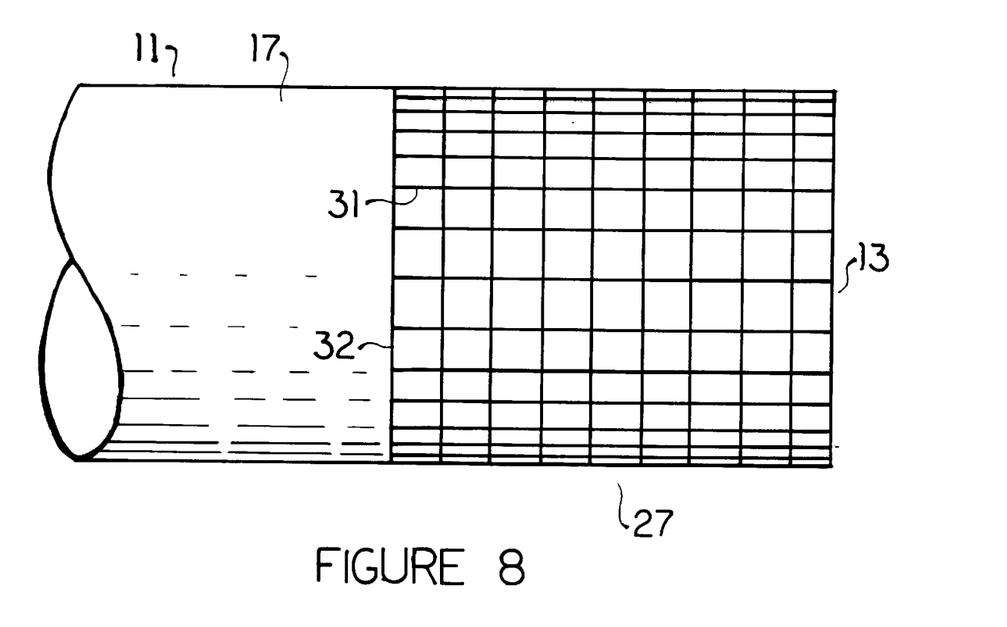
FIG. 8 is a plain elevational view taken of an end of a glass cylinder with the exterior surface prepared in accordance with the principles relating to the present invention with a rectangular pattern of grooves.

It is also considered that both a prepared interior surface 25 and a prepared exterior surface 27 of a glass cylinder 11 for deposition of platinum alloy upon either end in manufacture of a biological conductivity testing cell 10 in accordance with the present invention may possess a uniform pattern of glass surface material removal by abrasion with respect to the axial and radial geometry of the glass cylinder as seen in FIG. 7 wherein a diamond pattern is effected with helical etching 30 in both directions of the exterior surface 17 of one end of a glass cylinder. A similar rectangular cross hatch pattern effected with axial etching 31 and radial etching 32 as seen in FIG. 8. In either case the etching 30–32 is uniform axially and radially and provides physical resistance against shear in displacement of the platinum alloy electrode 12 with respect to the glass cylinder 11, even if the areas between the substantially linear etchings 30–32 is left unabraded.

It is preferred that the etchings 30–32 be an addition to fully abraded exterior and interior surfaces 17, 15 adjacent the end surface 13 of the glass cylinder 11 so that the entire deposition surface is virgin and ensured to be free of contaminants. In this case the etchings 30–32 provide resistance to shear acting upon the platinum alloy deposition comprising the electrodes 12 which is in addition to the resistance against shear provided by the peaks 37 and valleys 35 of a prepared exterior or interior surface 27, 25 possessing a uniformly rough texture in comparison with the unprepared exterior and interior glass surfaces 17, 15. For the same reason that knurling, which is typically comprised of opposed helical etchings 30 or a rectangular cross hatch pattern of axial and radial etchings 31, 32 similar to that seen in FIGS. 7 & 8, is effective in providing a grip upon an otherwise smooth and hence slippery cylinder an etching 30–30 possessing radial and axial symmetry is both easily effected and effective in providing a grip upon the glass cylinder 11 by the electrode 12.

Figure 9:
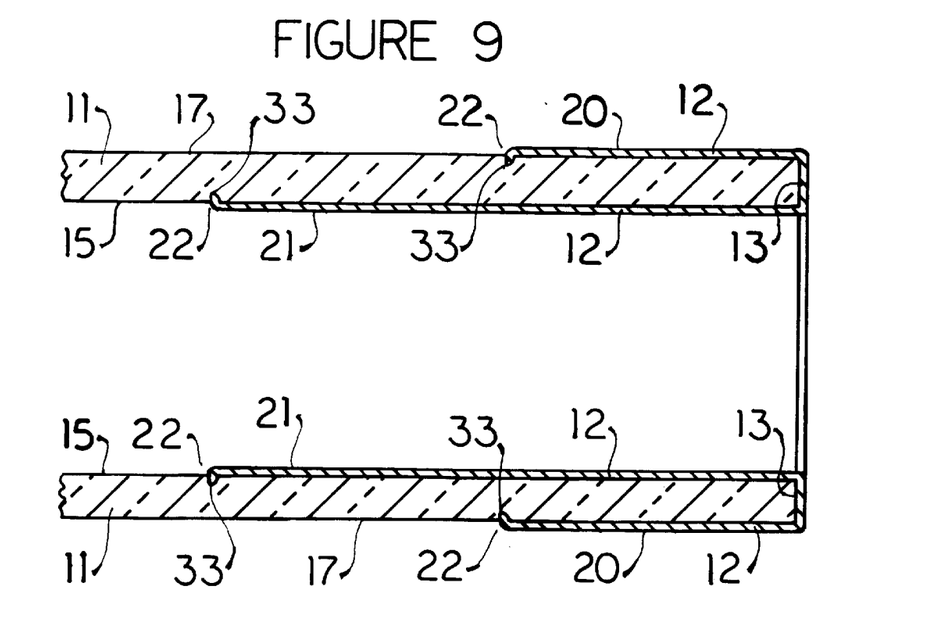
FIG. 9 is a cross sectional view of an end of a biological conductivity testing cell in accordance with the principles relating to the present invention having the exterior and interior edges of the electrode each located in an annular groove.

It is further noted in this regard that the two annular grooves 33 as seen in FIG. 9 are indeed radially and axially symmetric if disposed equidistantly upon each end of the glass cylinder 11. While there is no axial component other than the width of the annular grooves 33, if that width is consistent and balanced by a similarly shaped and located annular groove 33 upon the other end of the glass cylinder 11, this is neutral with regard to the conductivity characteristics of a testing cell 11.

It is also observed, with regard to the annular grooves 33 depicted in FIG. 9, that this very simple addition not only provides against axial shear by virtue of the two apposed radial walls to each groove 33 but also, if appropriately located to coincide with the electrode ends 22, protects the same against shear even if, as in the case depicted in FIG. 9, the electrode exterior surface 20 including that of the electrode end 22 extends outwardly beyond the glass exterior surface 17. This protection against the most salient area of concern is the result of physical proximity of the electrode edge 22 to the apposed walls of the annular groove 33 and the fact that the platinum alloy is solid, i.e. non-friable, with respect to the glass cylinder 11 and that any delamination will occur between the two rather than within either. The electrode ends 22, being each located at least partly within the two apposed walls of the annular groove 33, are each held immobile against axial shear against this most important area of the electrode 12.

Figure 10:
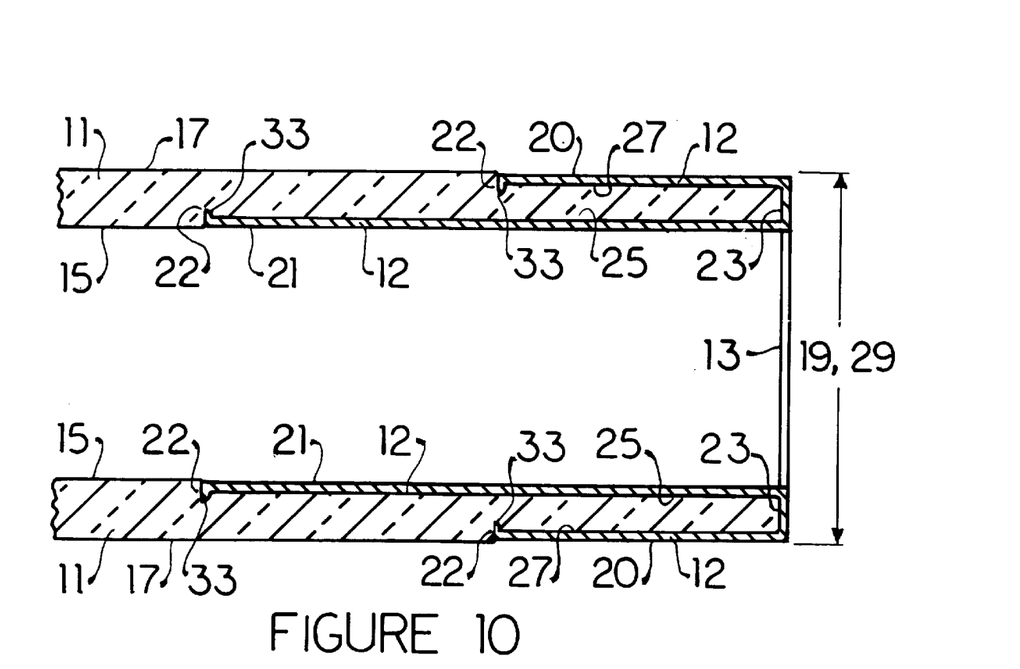
FIG. 10 is a cross sectional view of an end of a biological conductivity testing cell in accordance with the principles relating to the present invention having the exterior and interior edges of the electrode each located in an annular groove of a depth greater than the glass surface material removed from the balance of the deposition surface.

This observation with regarded to an annular groove 33 is extended in relation to FIG. 10 to fully prepared interior and exterior surfaces 25, 27 similar to that discussed above in relation to FIG. 4 in a manner similar to the discussion above in relation to FIGS. 7 & 8. The benefit of both the increased resistance to shear in any direction provided by the peaks 37 and valleys 35 of a uniformly rough prepared interior, exterior, or end surface 25, 27, 23 and the ensurance of a virgin deposition surface are again recognized. And the depth of the annular groove 33 is clearly seen in FIG. 10 to exceed the surface removal depth 39 and hence provides the same benefits of the annular groove 33 alone in protecting against axial displacement of the electrode end 22 with respect to the glass cylinder 11 which is considered to be the greatest particular concern in separation of an electrode 12 from the underlying glass cylinder 11.

It is emphasized that this concerns both electrode ends 22 upon both the electrode exterior and interior surfaces 20, 21, i.e. all four electrode ends 22, on each testing cell 10 and that all the aspects discussed above are considered beneficial in the same fundamental manner in providing resistance against shear in displacement of the platinum alloy deposition comprising an electrode 12 with respect to the glass cylinder 11 underlying.

The deposition of the platinum alloy coating comprising an electrode 12 is by conventional means specifically inclusive of, and preferably by, vapor deposition. This is as opposed to electroplating, primarily, which is considered a good alternative particularly with regard to electrodes 12 upon a biological conductivity testing cell 11 in accordance with the principles relating to the present invention, because electroplating results in a thicker coating, i.e. a greater deposition thickness 40, than vapor deposition and it is considered that one reason vapor deposition is generally regarded as the typical deposition means in conventional practice is the anticipated disposal of conventional biological testing cells. A biological testing cell 10 in accordance with the principles relating to the present invention possesses protection against shear in displacement of the platinum alloy deposition and hence deterioration of the electrodes 12 consequent to normal use including autoclaving as part of the operation cycle. Electroplating provides a greater deposition thickness 40 which is considered wasteful in a disposable product but which is considered feasible with a non-disposable product.

Vapor deposition of the platinum alloy comprising the electrodes 12 of a testing cell 10 in accordance with the principles relating to the present invention, however, is still preferred and is considered the conventional means of deposition and, more specifically, what is commonly known as chemical-vapor plating in which "a film is deposited when a metal-bearing gas thermally decomposes on contact with the heated surface of the base material" (*Materials Handbook*, 13 th Edition, McGraw-Hill, Inc., p. 879; under 'Vapor Deposited Coatings' pp. 878–879). This is opposed to other methods of vapor deposition suited to other materials.

It was also previously mentioned that the glass cylinder 11 suited to use in a testing cell 10 in accordance with the principles relating to the present invention is of a conventional composition and manufacture. While a tremendous variety of glasses are known, many of which are considered suitable, borosilicate glasses, which are conventionally utilized for laboratory glassware, are considered the best for the same reasons that these glasses are so utilized: "excellent chemical durability, for resistance to heat and thermal shock, and for low coefficients of thermal expansion" (Idid., p. 377, under Glass, pp. 376–383). These characteristics are largely in contrast to the most common and inexpensive glass known, i.e. bottle glass or soda-lime glass. Leaded glasses have poor acid resistance and high electrical conductivity and are considered unsuitable for these reasons. At the other end of the spectrum of glasses it is recognized that 100% silicon dioxide, either occurring naturally and known as quartz glass or fused quartz, or industrially made and known as fused silica glass, does not provide any known benefit over much less expensive and much more easily manufactured borosilicate glasses.

And with further regard to materials, it has also been previously mentioned that conventional platinum alloys are considered the best for the pair of opposed electrodes 12 deposited upon the ends of a glass cylinder 11 which has had surfaces prepared with abrasion to provide a virgin surface and physical resistance to shear. And, again, the reasons are substantially the same ones for which platinum alloys are commonly utilized in laboratory equipment including the unique catalytic qualities of platinum which is considered too soft to be utilized alone without alloying. The preferred alloying element is iridium, further preferably alloyed with platinum in a 5–30 percent range, most preferable in a 10–20 percent range, which is opposed to 95–70 per cent and 90–80 percent platinum, respectively. There is a trade off, essentially, between electrical properties and hardness with an increase in alloying percentage resulting in decreased conductivity and increased hardness. Osmium and rhodium, which are in the same metal group as platinum along with iridium are also considered good alternative alloying metals which do not greatly diminish conductivity, substantially improve hardness, and do not affect the unique catalytic characteristics of platinum.

The preparation of the end and adjacent interior and exterior surfaces 13, 15, 17 of a glass cylinder 11 prior to deposition of platinum alloy to form the electrodes 12 on a biological conductivity testing cell 10 in accordance with the principles relating to the present invention has been discussed previously discussed at length extensively in both the discussion of the principles and the detailed embodiment above and the conventional nature of the abrading, appropriately selected from among various forms in accordance with the geometry imposed by the surfaces 13, 15, 17 concerned upon the glass cylinder 11 and the specific form of glass surface removal desired, e.g. the prepared end, interior, and exterior surfaces 23, 25, 27, and the area encompassed and depth desired, e.g. pattern etching 30–30, annular groove 33 and fully contiguous deposition area of a uniform surface roughness of valleys 35 and peaks 37 all of which provide similar benefits for the manifold and fundamentally similar reasons discussed at length above.

With regard to usage of a biological testing cell 10 in accordance with the principles relating to the present invention, as mentioned previously, it is intended that a biological sample be held therein and a weak alternating current passed therethrough for the purpose of measuring, i.e. monitoring, impedance. Changes in impedance are associated with metabolic activity. The rate of change in impedance, and hence in metabolic activity, is of particular concern. Normal tissue, cells, and genetic material, i.e. DNA components and compounds including purines, pyrimidines, nucleic acids, nucleoprotein, nucleosides, nucleosomes, and nucleotides, are all characterizable by having a normal rate of metabolic activity. Abnormal or cancerous tissue, cells, and genetic material are all characterizable by elevated metabolic activity in comparison with a normal rate of metabolic activity.

The replication of genetic material is of greatest interest and monitoring the same with the monitoring of the impedance of a weak alternating current through a biological conductivity testing cell 10 in accordance with the principles relating to the present invention is of particular interest. It is observed that tissue growth is dependent upon the growth of cells and that cell growth requires cell division which requires replication of genetic material. Genetic material can be replicated in at least several different manners: (a) cell division in which genetic material native to that cell is replicated; (b) cell division in which genetic material both foreign and native to that cell is replicated; and (c) polymerase chain reaction. The first is natural and requires only a simple, substantially unalterated, biological sample. The second is typically done with a plasmid containing the foreign genetic material being introduced to a cell. Bacterial cells are typically utilized for plasmid introduction and *E. Coli* is the most commonly utilized bacteria. The third requires a portion of DNA, typically an oligonucleotide, which has either been isolated from a natural source or synthetically produced.

Synthetic nucleotides, which include synthetic oligonucleotides, are commercially available for replication using polymerase chain reaction. Being synthetically produced, however, these nucleotides are expensive and a single synthetic oglionucleotide is typically replicated in a geometric progression with thermal cycling. The dual strands of DNA are split in denaturing caused by elevation of temperature above 90 degrees C and the reverse of this, i.e. binding of opposed strands, or portions of strands, of DNA is achieved with lowering the temperature to about 40 degrees C. A synthetic nucleotide having a known structure is placed in a biological sample comprised of wild type DNA and during the first thermal cycle combines with a congruent portion of the denatured DNA.

Denaturing in the second thermal cycle splits this dual stranded DNA portion into two complementary segments or oligonucleotides and results in each combining with a complementary segment of another denatured DNA strand. The third cycle achieves eight complementary oligonucleotides each reflecting the known structure of the synthetic oligonucleotide which is replicated in this manner. Thermal cycling can be continued to provided approximately ten thousand replicates of the original, typically synthetic, genetic material of interest. The monitoring of this replication of genetic material is achieved with monitoring of the impedance of a weak alternating current passed through a biological conductivity testing cell 10 in accordance with the principles relating to the present invention in the same manner as normal tissue growth, abnormal tissue growth, normal cell division, and abnormal cell division.

A plug must be disposed in each end of the testing cell 10 to seal the interior containing the biological sample and bounded by the glass interior surface 15 and the plug which typically also covers the end of the electrode 12 with electrical contact being made between contacts providing the monitored alternating current and a portion of the electrode exterior surface 20. The electrode 12 must be in communication with the biological sample and hence includes an electrode interior surface 21, which as mentioned before, is typically longer than the portion of the electrode exterior surface 20, but the portion of the electrode 12 immediately adjacent to the prepared end surface 23 simply provides the necessary connection between electrode interior and exterior surfaces 21, 20.

The foregoing is intended to provide one skilled in the art with the best known manner of making and using an embodiment in accordance with the principles relating to the present invention and is not to be interpreted in any manner as restrictive of that invention or the rights and privileges secured by Letters Patent in protection of the same for which.

I claim:

1. A biological conductivity testing cell, intended for holding a biological sample through which a weak alternating current is passed and the impedance of that current monitored, said biological conductivity testing cell comprising:
   a glass cylinder possessing two opposed ends each having an electrode disposed thereupon;
   said glass cylinder possessing an exterior surface, an interior surface, and two opposed substantially parallel end surfaces;
   a portion of each of two combined surfaces, each including said end surface and the interior and exterior surfaces adjacent to each said end surface, possessing a virgin deposition surface of substantially uniform roughness resulting from glass surface material removed by abrasion;
   said electrodes each comprising a coating of platinum alloy deposited upon each said combined surface having glass surface material removed therefrom by abrasion;
   wherein the substantially uniform roughness of said deposition surface provides physical resistance against shear in displacement of each said electrode from said glass cylinder.

2. A biological conductivity cell in accordance with claim 1 wherein said coating of platinum alloy deposited upon said interior surface of said glass cylinder possesses a greater axial length than said coating of platinum alloy deposited upon said exterior surface of said glass cylinder.

3. A biological conductivity cell in accordance with claim 1 wherein said coating of platinum alloy is deposited with chemical-vapor plating.

4. A biological conductivity cell in accordance with claim 1 wherein said platinum alloy is comprised of an alloy of platinum and one metal taken from the same metal group including osmium, rhodium, and iridium.

5. A biological conductivity cell in accordance with claim 4 wherein said platinum alloy is comprised of an alloy of platinum and iridium.

6. A biological conductivity cell in accordance with claim 5 wherein said platinum alloy is comprised of an alloy of between 70–95 percent platinum and 30–5 percent iridium.

7. A biological conductivity cell in accordance with claim 1 wherein said virgin deposition surface of substantially uniform roughness resulting from glass surface material removed by abrasion includes an etching which is radially and axially uniform.

8. A biological conductivity cell in accordance with claim 7 wherein said etching possesses a diamond pattern.

9. A biological conductivity cell in accordance with claim 7 wherein said etching possesses a rectangular pattern.

10. A biological conductivity cell in accordance with claim 1 wherein said virgin deposition surface of substantially uniform roughness resulting from glass surface material removed by abrasion includes at least one annular groove which is radially and axially uniform.

11. A biological conductivity cell in accordance with claim 10 wherein each said electrode possesses an edge located in one said annular groove.

12. A biological conductivity cell in accordance with claim 11 wherein each said electrode possesses an interior edge and an exterior edge each located in one said annular groove.

13. A biological conductivity cell in accordance with claim 1 wherein said virgin deposition surface of substantially uniform roughness resulting from glass surface material removed by abrasion encompasses all of said portion of said interior surface of said glass cylinder adjacent to said end surface of said glass cylinder upon which platinum alloy is deposited.

14. A biological conductivity cell in accordance with claim 13 wherein said virgin deposition surface of substantially uniform roughness resulting from glass surface material removed by abrasion further includes an annular groove which is radially and axially uniform in which an electrode edge is located.

15. A biological conductivity cell in accordance with claim 13 wherein each said platinum alloy deposition possesses a substantially uniform thickness and said virgin deposition surface of substantially uniform roughness resulting from glass surface material removed by abrasion encompassing all of said portion of said interior surface of said glass cylinder adjacent to said end surface of said glass cylinder upon which platinum alloy is deposited possesses a surface removal depth which is not exceeded by said substantially uniform thickness of said platinum alloy deposition.

16. A biological conductivity cell in accordance with claim 15 wherein each said platinum alloy deposition possesses a substantially uniform thickness substantially equivalent to said surface removal depth and said electrode possesses an interior surface which is substantially flush with the portion of said interior surface of said glass cylinder immediately adjacent an interior edge of said electrode.

17. A biological conductivity cell in accordance with claim 1 wherein said virgin deposition surface of substantially uniform roughness resulting from glass surface material removed by abrasion encompasses all of said portion of said exterior surface adjacent to said end surface upon which platinum alloy is deposited.

18. A biological conductivity cell in accordance with claim 17 wherein said virgin deposition surface of substantially uniform roughness resulting from glass surface material removed by abrasion further includes an annular groove which is radially and axially uniform in which an electrode edge is located.

19. A biological conductivity cell in accordance with claim 17 wherein each said platinum alloy deposition possesses a substantially uniform thickness and said virgin deposition surface of substantially uniform roughness resulting from glass surface material removed by abrasion encompassing all of said portion of said exterior surface of said glass cylinder adjacent to said end surface of said glass cylinder upon which platinum alloy is deposited possesses a surface removal depth which is not exceeded by said substantially uniform thickness of said platinum alloy deposition.

20. A biological conductivity cell in accordance with claim 19 wherein each said platinum alloy deposition possesses a substantially uniform thickness substantially equivalent to said surface removal depth and said electrode possesses an interior surface which is substantially flush with the portion of said exterior surface of said glass cylinder immediately adjacent an exterior edge of said electrode.

21. A biological conductivity cell in accordance with claim 1 wherein said biological sample through which a weak alternating current is passed and the impedance of that current monitored contains genetic material and replication of said genetic material is reflected by changes in said impedance.

22. A biological conductivity cell in accordance with claim 21 wherein said biological sample through which a weak alternating current is passed and the impedance of that current monitored contains at least one live cell and division of said cell is reflected by changes in said impedance.

23. A biological conductivity cell in accordance with claim 22 wherein said biological sample through which a weak alternating current is passed and the impedance of that current monitored contains tissue suspected of being cancerous and the rate of cell division is reflected by said changes in impedance.

24. A biological conductivity cell in accordance with claim 1 wherein said biological sample through which a weak alternating current is passed and the impedance of that current monitored contains genetic material which undergoes replication induced by thermal cycling.

25. A biological conductivity cell in accordance with claim 24 wherein said genetic material contained in said biological sample through which a weak alternating current is passed and the impedance of that current monitored which undergoes replication induced by thermal cycling includes at least one oligonucleotide.

26. A biological conductivity cell in accordance with claim 25 wherein said genetic material contained in said biological sample through which a weak alternating current is passed and the impedance of that current monitored which undergoes replication induced by thermal cycling includes at least one said oligonucleotide is synthetic.

27. A biological conductivity cell in accordance with claim 24 wherein said genetic material contained in said biological sample through which a weak alternating current is passed and the impedance of that current monitored which undergoes replication induced by thermal cycling includes at least one living cell.

28. A biological conductivity cell in accordance with claim 27 wherein said genetic material contained in said biological sample through which a weak alternating current is passed and the impedance of that current monitored which undergoes replication induced by thermal cycling includes at least one living bacterial cell.

29. A biological conductivity cell in accordance with claim 28 wherein said genetic material contained in said biological sample through which a weak alternating current is passed and the impedance of that current monitored which undergoes replication induced by thermal cycling includes a plasmid containing genetic material foreign to said bacterial cell.

30. A biological conductivity cell in accordance with claim 29 wherein said genetic material contained in said biological sample through which a weak alternating current is passed and the impedance of that current monitored which undergoes replication induced by thermal cycling includes a plasmid containing synthetic genetic material foreign to said bacterial cell.

* * * * *